United States Patent [19]

Cavalla et al.

[11] 4,028,365

[45] June 7, 1977

[54] BENZ[g]INDOLYL COMPOUNDS

[75] Inventors: John Frederick Cavalla, Isleworth; John Leheup Archibald, Windsor, both of England

[73] Assignee: John Wyeth & Brother Limited, Maidenhead, England

[22] Filed: Nov. 15, 1974

[21] Appl. No.: 524,005

Related U.S. Application Data

[63] Continuation-in-part of Ser. No. 323,684, Jan. 15, 1973, abandoned, which is a continuation-in-part of Ser. No. 175,345, Aug. 26, 1971, abandoned.

[30] Foreign Application Priority Data

Sept. 3, 1970 United Kingdom ............ 42090/70
July 22, 1971 United Kingdom ............ 34376/71

[52] U.S. Cl. .................... 260/293.61; 260/293.77; 260/295 Q; 260/295 AM; 424/267
[51] Int. Cl.² ....................................... C07D 471/02
[58] Field of Search .............................. 260/293.61

[56] References Cited

UNITED STATES PATENTS

| | | | |
|---|---|---|---|
| 3,498,984 | 3/1970 | Santilli et al. ............... | 260/256.5 R |
| 3,527,761 | 9/1970 | Archibald et al. ............ | 260/293.61 |

FOREIGN PATENTS OR APPLICATIONS

| | | | |
|---|---|---|---|
| 772,190 | 1/1972 | Belgium | |
| 1,582,086 | 8/1969 | France ......................... | 260/293.61 |
| 2,144,080 | 3/1972 | Germany ...................... | 260/293.61 |

*Primary Examiner*—Natalie Trousof
*Attorney, Agent, or Firm*—Arthur E. Wilfond

[57] ABSTRACT

A group of benz[g]indolyl compounds useful in the treatment of disorders and diseases of the cardiovascular system is described. These are piperidine compounds linked by the nitrogen atom to a substituted or unsubstituted benz[g]indolyl radical through the intermediary of a lower-alkylene radical. The piperidine rings are further substituted by an acylamino residue.

2 Claims, No Drawings

BENZ[g]INDOLYL COMPOUNDS

This invention relates to benz(g)indolyl compounds and is a continuation-in-part of our copending application Ser. No. 323,684 filed Jan. 15, 1973 and entitled "Heterocyclic Compounds" and now abandoned which is a continuation-in-part of our application Ser. No. 175,345 filed Aug. 26, 1971 entitled "Pharmaceutical Compositions" and now abandoned.

The invention provides a benz(g)indole compound of the general formula:

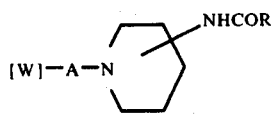  (I)

wherein W represents a radical selected from benz[g]indolyl and benz[g]indolyl substituted by lower alkyl, A represents a lower alkylene radical of 1 to 4 carbon atoms, R represents a radical selected from phenyl and phenyl substituted by halogen, lower alkoxy or lower alkyl, and the pharmaceutically acceptable acid addition salts thereof.

It is to be understood that the term "alkylene" used herein includes both straight and branched chain radicals.

The compounds of formula (I) and the pharmaceutically acceptable acid addition salts thereof exhibit pharmacological activity for example one or more of the following activities:
action on the cardiovascular system (such as hypotensive and/or anti-hypertensive and/or peripheral vasodilation and/or anti-anginal and/or anti-arrhythmic activity), and sometimes central nervous system activity (such as sedative or anti-convulsant activities) when tested on warm blooded animals.

In addition to having useful pharmaceutical properties as mentioned above the novel compounds of the invention are intermediates for the preparation of other compounds of formula I.

W is a benz[g]indolyl (for example 3-benz[g]indolyl) radical, which may be substituted by lower alkyl (for example methyl, ethyl, propyl or n, s and t-butyl).

Examples of R are unsubstituted phenyl or phenyl substituted by one or more groups, which may be the same or different selected from halogen (for example fluorine, chlorine or bromine), lower alkyl (for example methyl, ethyl, propyl, or n, s and t-butyl and lower alkoxy (for example methoxy, ethoxy, propoxy or butoxy).

Examples of A are methylene, ethylene, propylene, methylethylene and butylene. Examples of acid addition salts are those formed from inorganic and organic acids in particular pharmaceutically acceptable acid addition salts such as the sulphate, hydrochloride, hydrobromide, hydroiodide, nitrate, phosphate, sulphonate (such as the methane-sulphonate and p-toluene-sulphonate), acetate, maleate, fumarate, tertrate and formate.

The compounds of general formula (I) can be prepared in a number of ways by building up the molecule from suitable starting materials in known manner. Such processes applied to the preparation of the novel compounds of formula (I) are included in the scope of the invention.

One method of preparation of compounds of general formula (I) comprises reacting a compound of the general formula

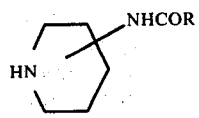  (III)

with an alkylating or acylating agent of the general formula

[W]-A-Y  (IV)

where R, W and A have the meanings already defined and Y is a halogen atom or an equivalent replaceable atom or radical, for example an organic sulphonyl radical such as tosyl radical.

The compounds of general formula (IV), are known compounds or can be made following the methods known for preparing compounds of these types. The starting materials of general formula III can generally be made by acylating a corresponding amino compound of the general formula

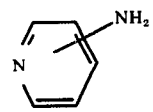  (VIII)

and if necessary reducing the ring system to the corresponding tetrahydropyridine or piperidine ring. The starting material of general formula III is preferably prepared by either (i) forming the oxime of an N-benzyl-4-piperidone, reducing to give the 4-amino compound, acylating the amino group and then hydrogenolysing the benzyl residue, or (ii) treating the pyridine of formula

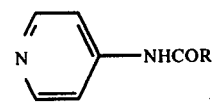  (IX)

with a benzyl halide, for example benzyl chloride to give the quaternary salt, reducing with an alkali metal borohydride to give the corresponding N-benzyl-tetrahydro-pyridine which is further subjected to concomitant de-benzylation and reduction of the 3,4-double bond by catalytic hydrogenation, or (iii) catalytic hydrogenation of compound (IX) in the presence of acetic anhydride to give

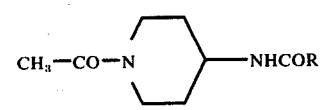  (X)

and then selectively hydrolysing the acetyl group.

The piperidine compounds of general formula (I) may be prepared by starting with a compound of formula:

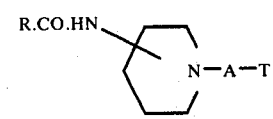  (XI)

wherein T is a known precursor group of W and reacting with another molecule of the type known in the literature for the formation of W. Reference may be made in this connection to standard textbooks of Organic Chemistry such as: Organic Chemistry by Paul Karrer (Elsevier Publishing Company, Inc., 1950); Organic Chemistry by Fieser & Fieser (Reinhold Publishing Corporation, 1956); Chemistry of Carbon Compounds by Rodd (Elsevier), Amsterdam, 1951–1969); Heterocyclic Compounds edited by Elderfield (John Wiley & Sons, Inc., 1950–1968); and Chemistry of the Heterocyclic Compounds edited by Weissberger (Interscience, 1954). As Examples of T may be mentioned —$CH_2.CH(OAlkyl)_2$ where Alkyl represents a lower alkyl radical. As examples of reactants known to react with T may be mentioned, 1-naphthyl-hydrazine. The compounds of formula XI may be made following methods known in the art for the preparation of similar compounds.

The reactions outline above usually are carried out in a solvent which is inert under the reaction conditions. The most suitable solvent system is chosen and varies depending on the particular reactants being employed. If necessary heating the reactants in solution under reflux can be carried out, and if necessary heating under high pressures may also be used.

Once a compound of general formula (I) has been prepared, then if necessary one or more substitutents in the molecule may be converted to another substituent each within its own meanings specified in connection with formula (I).

If a compound of formula (I) is produced in which the —COR group is other than that desired if necessary this may be hydrolysed to the corresponding compound of formula (I) containing a free amino group instead of NHCOR and this may then be reacted with an acylating agent to give a compound of formula (I) with different —COR group.

Compounds of formula I in which A is a branched chain alkylene radical possess an asymmetric carbon atom and are therefore capable of existing in optically active stereo isomeric forms. The optical isomers may be separated by standard resolution procedures. For instance the compounds contain a basic nitrogen atom and may generally be resolved by treatment with a suitable optically active acid. Optically active acids are described in the literature and suitable ones for the resolution of any particular compound are chosen by experiment.

If necessary, in any of the reactions hereinbefore described, reactive substituent groups may be blocked during a reaction and released at a later stage. As already indicated the novel piperidine compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide).

The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

The compounds of the invention may be used in pharmaceutical compositions which contain as active ingredients a compound of formula (I) as hereinbefore defined, which may be micronised. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets, and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances a compound is orally active and can be administered orally either in liquid or solid composition form.

Preferably the pharmaceutical compositions is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following non-limiting Examples illustrate the invention:

EXAMPLE 1

1-[2-(3-Benz[g]indolyl)ethyl]-4-benzamidopiperidine a. 4-Benzamidopiperidine (62 g.) was added to a stirred suspensions of 1.1 g. cupric acetate and 9.5 g. paraformaldehyde in 300 ml. dry dioxane, followed by propiolaldehyde diethylacetal (38.6 g.). Stirring was continued for 24 hours at 80° C under nitrogen. The hot reaction mixture was filtered and the filtrate was evaporated. Recrystallisation of the solid residue from ethyl acetate-petroleum ether (bp. 60°–80° C) gave 4-benzamido-1-(4,4-diethoxybut-2-ynyl)piperidine as colourless shining leaflets. (84.6 g.), m.p. 130° C. (Found: C, 69.5; H, 8.3; N, 8.3 $C_{20}H_{28}N_2O_3$ requires C, 69.7; H, 8.2; N, 8.1%).

b. The foregoing product (70 g.) in absolute ethanol (1 l.) was hydrogenated in the presence of 10% palladium-on-carbon (7 g.) at 50 p.s.i. hydrogen pressure for 30 minutes. Evaporation of the filtrate after removing the catalyst, and recrystallisation of the residue from petroleum ether (b.p. 60°–80° C) gave 1-(4,4-diethoxybutyl)-4-benzamidopiperidine as colourless leaflets (61.29 g.) m.p. 95° C. (Found: C, 69.0; H, 9.2; N, 8.2. $C_{20}H_{32}N_2O_3$ requires C, 68.9; H, 9.3; N, 8.0%).

c. 1-(4,4-diethoxybutyl)-4-benzamidopiperidine (3.48 g.) was added portionwise to a solution of 1-naphthylhydrazine hydrochloride (1.95 g.) in 25% aqueous acetic acid (15 ml.) with stirring at 80° C. Stirring and heating were continued for 2.5 hours, then the mixture was left for 3 days at room temperature to precipitate the crude product (1.28 g.). Recrystallisation from ethanol gave the title compound as the hydrochloride, hemihydrate, m.p. 285° C (dec.) (Found: C, 70.2; H, 6.75; N, 9.2; $C_{26}H_{27}N_3O.HCl.½H_2O$ requires C, 70.5; H, 6.6; N, 9.3%.)

The product exhibited marked hypotensive activity. It also had depressant activity.

EXAMPLE 2

1-[4-(3-Benz[g]indolyl)butyl]-4-(p-chloro)benzamidopiperidine 1-(6,6-diethoxyhexyl)-4-(4-chloro)benzamidopiperidine [prepared from 6,6-diethoxyhexyl bromide and 4-(4-chloro) benzamidopiperidine] are added to a solution of 1-naphthyl-hydrazine hydrochloride in 25% aqueous acetic acid with stirring at 80° C. The reaction mixture is heated at 80° for 3 hours, then it is worked up in a similar manner to Example 1 to give the title compound as a hydrochloride.

EXAMPLE 3

1-[2-(2-Ethyl-3-benz[g]indolyl)ethyl]-4-(3-methoxy)-benzamidopiperidine

A mixture of 4-(3-methoxy)benzamidopiperidine, 2-ethyl-3-(2-bromoethyl)-benz[g]indole, and powdered potassium carbonate are stirred at 100° for 1 hour. Working up in the manner described in Example 1 provides the title compound which is isolated as a hydrochloride after treatment with ethanolic HCl.

EXAMPLE 4

1-[2-(1-Methyl-3-benz[g]indolyl)ethyl]-4-(2-methyl)-benzamidopiperidine

The product of Example 1 is hydrolysed by heating with aqueous ethanolic NaOH to give 1-[2-(3-benz[g]indolyl)ethyl]-4-aminopiperidine. This is added to sodamide in liquid ammonia and treated with 1 equivalent of methyl iodide to give 1-[2-(1-methyl-3-benz[g]indolyl)ethyl]-4-aminopiperidine. The foregoing intermediate in methylene dichloride is stirred with potassium carbonate in $H_2O$ at 5° while o-toluoyl chloride is added dropwise. The product is isolated in the manner described in Example 1 and treated with ethanolic HCl to give the title compound as a hydrochloride.

Tests for action on the cardiovascular system were conducted according to one of the following procedures.

Hypotensive and/or anti/hypertensive activity

Method 1 (Rat)

Rats were anaesthetised with pentobarbitone sodium (60 mg/kg) and the jugular vein, trachea and carotid artery were cannulated. The test compound was given intravenously at 15 min. intervals (dose range 0.8–25.6 mg/kg cumulative) and blood pressure and heart rate were recorded via the carotid artery at 30 second and 15 minutes after administration. The production of a fall of 30 mm. mercury in diastolic pressure from control values was considered to be significant hypotensive activity. A decrease in heart rate of more than 30% from control values was considered to be significant bradycardia.

Method 1 (Cat)

Cats were anaesthetised with pentobarbitone sodium (30 mg/kg) and the cephalic vein, femoral and carotid arteries and trachea were cannulated. The carotid cannula was introduced into the left ventricle and the femoral cannula into the aorta. Blood pressure and heart rate were recorded from the aortic cannula and left ventricular pressure from the carotid cannula. The test compounds were administered intravenously (0.1–25.6 mg/kg).

Method 2 (hypertensive rats)

Male or female rats were rendered hypertensive by applying a figure of 8 ligature around one kidney and contralateral nephrectomy. Blood pressure stabilises at a hypertensive level after 6 weeks. Systolic pressure is measured indirectly using a Decker Caudal Plethysmograph. A control group of rats is run with each group treated with drug. Each group usually consists of six rats. Drugs are usually administered by the IP or oral routes. Pressures are read prior to drug administration and at two and 24 hours thereafter.

Activity in either method 1 (rats or cats) or method 2 was considered to indicate hypotensive activity.

We claim:

1. A benz[g]indole compound of the formula

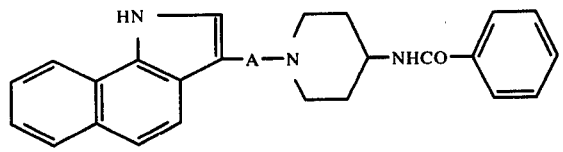

where A is lower alkylene of 1 to 4 carbon atoms, and the pharmaceutically acceptable acid addition salts thereof.

2. 1-[2-(3-benz[g]-indolyl)ethyl]-4-benzamidopiperidine and pharmaceutically acceptable acid addition salts thereof.

* * * * *